(12) United States Patent
Gutman et al.

(10) Patent No.: US 7,002,016 B2
(45) Date of Patent: Feb. 21, 2006

(54) PROCESS FOR THE PREPARATION OF THREO-METHYLPHENIDATE HYDROCHLORIDE

(75) Inventors: Arie Gutman, Haifa (IL); Igor Zaltsman, Haifa (IL); Anton Shalimov, Haifa (IL); Maxim Sotrihin, Haifa (IL); Gennady Nisnevich, Haifa (IL)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 10/793,600

(22) Filed: Mar. 4, 2004

(65) Prior Publication Data
US 2004/0176412 A1 Sep. 9, 2004

Related U.S. Application Data

(60) Provisional application No. 60/452,724, filed on Mar. 7, 2003.

(51) Int. Cl.
*C07D 221/02* (2006.01)
(52) U.S. Cl. ........................ 546/183; 546/237
(58) Field of Classification Search ............... 546/237, 546/183
See application file for complete search history.

(56) References Cited

U.S. PATENT DOCUMENTS 6,531,055 B1 * 3/2003 Greaney ..................... 208/263

FOREIGN PATENT DOCUMENTS

WO  WO 99/36403  * 7/1999

OTHER PUBLICATIONS

Axten et al. "A stereoselective . . . " J. Org. Chem. 64, p. 9628-6929 (1998).*
Sirovskii et al. "Dehydrochlorination . . . " CA 105:152291 (1986).*
Belokon et al. "Enantiomerically enriched . . . " CA 131: 199943 (1999).*
Prashad et al. "An efficient large scale . . . " CA 132:49864 (1999).*

* cited by examiner

Primary Examiner—Celia Chang
(74) Attorney, Agent, or Firm—William J. Davis; Imre Balogh

(57) ABSTRACT

The present invention provides a process for the preparation of threo-methylphenidate hydrochloride. According to a preferred embodiment, the process comprises the following steps:

(a) contacting 1-(phenylglyoxylyl)piperidine arenesulfonylhydrazone of the formula

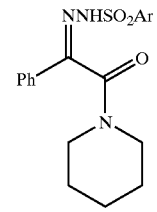

wherein Ar denotes an aryl group, where the aryl group may be substituted by a $C_1$–$C_6$ alkyl, halo or nitro group;
with an inorganic base in the presence of a water immiscible organic solvent and a phase transfer catalyst to obtain ($R^*,R^*$)-enriched 7-phenyl-1-azabicyclo [4.2.0]octan-8-one of the formula:

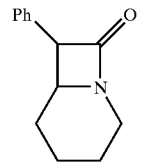

(b) reacting the ($R^*,R^*$)-enriched 7-phenyl-1-azabicyclo [4.2.0]octan-8-one prepared in step (a) with a solution of hydrogen chloride in methanol to obtain threo-enriched methylphenidate hydrochloride;
(c) crystallizing the threo-enriched methylphenidate hydrochloride prepared in step (b) to give the desired threo-methylphenidate hydrochloride. Preferably, the threo-methylphenidate hydrochloride produced by the process of the present invention contains no more than 1% of the erythro-isomer.

6 Claims, No Drawings

PROCESS FOR THE PREPARATION OF THREO-METHYLPHENIDATE HYDROCHLORIDE

This application claims the benefit of Provisional Application No. 60/452,724, filed on Mar. 7, 2003.

FIELD OF THE INVENTION

The present invention relates to a process for the preparation of threo-methylphenidate hydrochloride.

LIST OF REFERENCES

The following references are considered to be pertinent for the purpose of understanding the background of the present invention:

J. M. Axten et al., J. Org. Chem., 1998, v.63, 9628–9 (and supporting information disclosed therein);
H. M. Deutsch et al., J. Med. Chem., 1996, v.39, 1201–9;
L. Panizzon, Helv. Chim. Acta, 1944, v. 27, 1748–56;
K. Patric et al., J. Labelled Compd. Radiopharm., 1982, v. 19, 485–90;
L. Szporny et al., Biochem. Pharmacol., 1961, v. 8, 263–8;
U.S. Pharmacopoeia
USP 26 "Methylphenidate Hydrochloride";
U.S. Pat. No. 2,507,631;
U.S. Pat. No. 2,838,519;
U.S. Pat. No. 2,957,880;
U.S. Pat. No. 5,936,091;
WO 99/36403; and
WO 01/27070.

BACKGROUND OF THE INVENTION

Racemic threo-methylphenidate or methyl (R*,R*)-α-phenyl-2-piperidineacetate, having the formula:

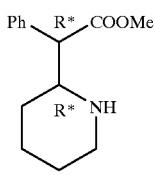

and its salts are CNS (central nervous system) stimulants that are chemically and pharmacologically similar to the amphetamines. threo-Methylphenidate's CNS actions are milder than those of the amphetamines and have more noticeable effects on mental activities than on motor activities.

Methylphenidate has two chiral centers, but the drug used in therapy comprises only the threo pair of d- and 1-enantiomers. Methylphenidate is marketed as a racemic mixture of 1-threo-methylphenidate and d-threo-methylphenidate, where the d-threo-Methylphenidate is considered to be more potent than the 1-threo-enantiomer.

A commercially available drug is sold under the name Ritalin™ (Novartis) and it consists of threo-methylphenidate in the form of the hydrochloride salt. This product is orally administered and clinically used in the treatment of attention-deficit hyperactivity disorders (ADHD) in children and used for the treatment of narcolepsy and depression in adults.

It has been reported by Szporny (1961) that among racemic mixtures of threo and erythro diastereomers of methylphenidate, only threo-isomer displays stimulant properties. In U.S. Pharmacopoeia USP 26 it is indicated that the content of erythro isomer in a racemic mixture of threo/erythro methylphenidate hydrochloride should not be higher than 1% in order to possess desired properties of active pharmaceutical ingredient (API).

Synthetic methods for the preparation of racemic mixtures of threo- and erythro-α-phenyl-2-piperidineacetamides as raw materials for the preparation of threo-methylphenidate were described in U.S. Pat. Nos. 2,507,631, 2,838,519, 2,957,880 and 5,936,091, in WO 01/27070 and by Panizzon (1944) and Patric (1982). These methods include using sodium amide as base in the nucleophilic substitution of chlorine in 2-chloropyridine with phenylacetonitrile followed by hydrolysis of the formed nitrile and reduction of the pyridine ring to a piperidine one by hydrogenation on PtO$_2$ catalyst to obtain erythro-enriched α-phenyl-2-piperidineacetamide, which is then subjected to epimerization, hydrolysis, and esterification of threo-ritalinic acid as shown in Scheme 1:

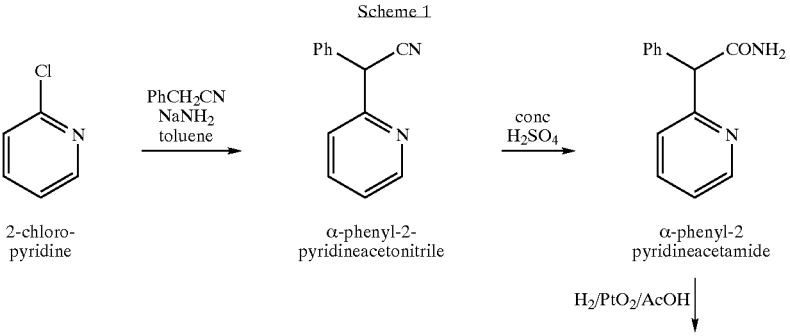

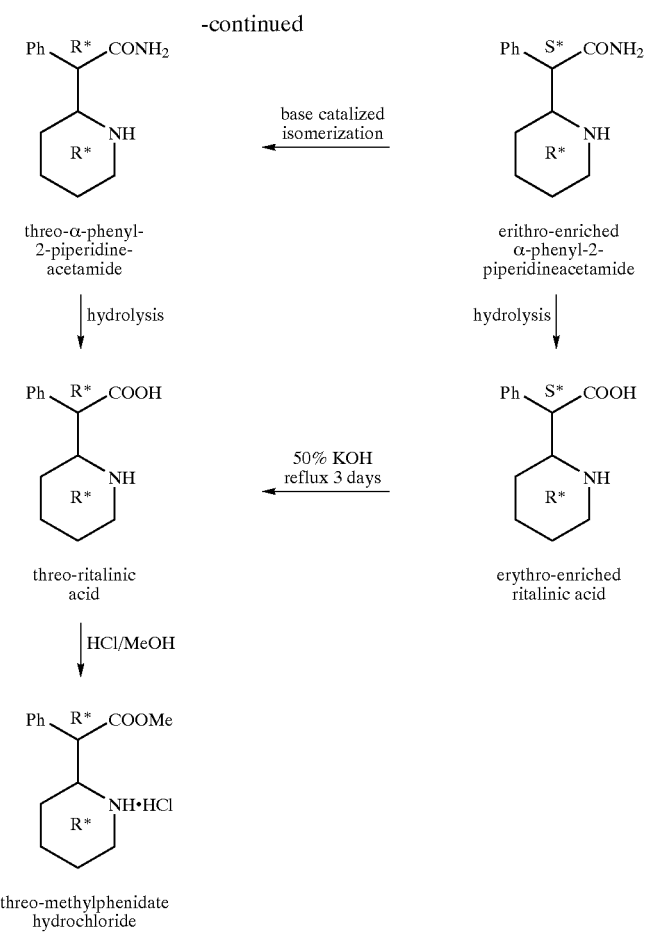

Alternatively, 2-bromopyridine was used instead of 2-chloropyridine by Deutsch (1996).

Other synthetic route for the preparation of threo-methylphenidate hydrochloride, as described by Axten (1998) and in WO 99/36403, is based on cyclization of easily available 1-(phenylglyoxylyl)piperidine arenesulfonylhydrazone to (R*,R*)-enriched 7-phenyl-1-azabicyclo[4.2.0]octan-8-one followed by conversion of the obtained β-lactam to threo-methylphenidate hydrochloride as described in Scheme 2:

Scheme 2

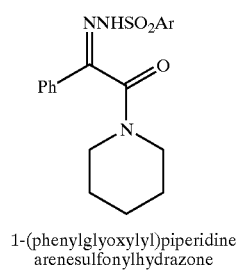

1-(phenylglyoxylyl)piperidine
arenesulfonylhydrazone

| t-BuOK

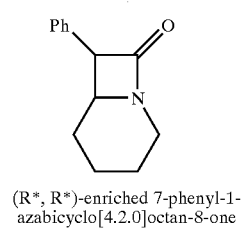

(R*, R*)-enriched 7-phenyl-1-
azabicyclo[4.2.0]octan-8-one

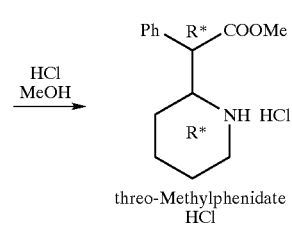

threo-Methylphenidate
HCl t-BuOK used in the first step of the synthesis described in Scheme 2 above is flammable and dangerous to handle in industrial-scale processes. In addition, the first step shown in Scheme 2 is expensive and the yield for obtaining the β-lactam product is relatively low (about 60%).

SUMMARY OF THE INVENTION

The present invention provides a simple and efficient process for the preparation of the hydrochloride salt of threo-methylphenidate, having high purity and in relatively high yields.

Thus, the process of the invention for the preparation of threo-methylphenidate hydrochloride comprises contacting 1-(phenylglyoxylyl) piperidine arenesulfonylhydrazone of the formula

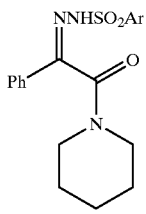

wherein Ar denotes an aryl group, where the aryl group may be substituted by a $C_1$–$C_6$ alkyl, halo or nitro group;

with an inorganic base in the presence of a water-immiscible organic solvent and a phase transfer catalyst to obtain (R*,R*)-enriched 7-phenyl-1-azabicyclo[4.2.0]octan-8-one of the formula:

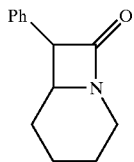

that is subsequently converted into threo-methylphenidate hydrochloride.

According to a preferred embodiment, the conversion into threo-methylphenidate hydrochloride comprises:
(i) reacting the (R*,R*)-enriched 7-phenyl-1-azabicyclo [4.2.0]octan-8-one with a solution of hydrogen chloride in methanol to obtain threo-enriched methylphenidate hydrochloride;
(ii) crystallizing the threo-enriched methylphenidate hydrochloride prepared in step (i) to give the hydrochloride salt of threo-methylphenidate.

The hydrochloride salt of threo-methylphenidate obtained in step (ii) preferably contains no more than 1% of the erythro-isomer.

The aryl group of 1-(phenylglyoxylyl)piperidine arenesulfonylhydrazone is an aromatic ring such as for example phenyl, p-tolyl, p-chlorophenyl or p-nitrophenyl group.

The phase transfer catalyst is selected from the group consisting of quaternary onium salts, crown ethers and polyglycols. In a preferred embodiment, the phase transfer catalyst is a quaternary ammonium salt or quaternary phosphonium salt. More preferably, the phase transfer catalyst is methyltrioctylammonium chloride.

According to another preferred embodiment of the invention, the phase transfer catalyst is a crown ether, for example, dibenzo-18-crown-6.

As mentioned above, the reaction is carried out in a water-immiscible organic solvent such as, for example, halogenated hydrocarbons, e.g. dichloromethane and aromatics, e.g. toluene.

The inorganic base is selected from sodium hydroxide, sodium carbonate, potassium carbonate or potassium hydroxide. The base may be added to the reaction mixture either in solid form or dissolved in an aqueous solution.

DETAILED DESCRIPTION OF THE INVENTION

The process for preparing threo-methylphenidate hydrochloride according to the present invention comprises reacting 1-(phenylglyoxylyl)piperidine arenesulfonylhydrazone in a water-immiscible organic solvent such as dichloromethane or toluene with a deprotonating aqueous solution comprising a base and a phase transfer catalyst, to form (R*,R*)-enriched 7-phenyl-1-azabicyclo[4.2.0]octan-8-one.

The inorganic base used in the process of the present invention is selected from sodium hydroxide, sodium carbonate, potassium carbonate or potassium hydroxide. Preferably the inorganic base is sodium hydroxide. The inorganic base may be in a solid form or in its aqueous solution.

The phase transfer catalyst (PTC) is used to carry the inorganic base from the aqueous phase or the solid phase into the organic phase. The phase transfer catalyst may be a quaternary onium salt, e.g. quaternary ammonium or phosphonium salts, a crown ether or polyglycol.

Non-limiting examples of suitable quaternary ammonium salts are: benzyltributylammonium bromide, benzyltributylammonium chloride, benzyltriethylammonium bromide, benzyltriethylammonium chloride, benzyltrimethylammonium chloride, didecyldimethylammonium chloride, dimethyldioctadecylammonium hydrogensulfate, dimethyldioctadecylammonium methosulfate, dodecyltrimethylammonium bromide, dodecyltrimethylammonium chloride, hexadecylpyridinium bromide, hexadecylpyridinium chloride, hexadecyltrimethylammonium bromide, methyltrioctylammonium chloride, phenyltrimethylammonium chloride, tetrabutylammonium bromide, tetrabutylammonium chloride, tetrabutylammonium hydrogensulfate, tetrabutylammonium hydroxide, tetrabutylammonium perchlorate, tetraethylammonium bromide, tetraethylammonium chloride, tetraethylammonium hydrogensulfate, tetraethylammonium hydroxide, tetrahexylammonium bromide, tetramethylammonium bromide, tetramethylammonium chloride, tetramethylammonium hydroxide, tetraoctylammonium bromide, tetrapropylammonium bromide, tetrapropylammonium chloride, tetrapropylammonium hydroxide, tributylethylammonium bromide, tributylmethylammonium chloride, tributylmethylammonium hydrogensulfate, trimethyloctadecylammonium bromide, trimethyloctadecylammonium chloride and trimethyltetradecylammonium bromide.

Non-limiting examples of quaternary phosphonium salts are: benzyltriphenylphosphonium bromide, benzyltriphenylphosphonium chloride, butyltriphenylphosphonium bromide, butyltriphenylphosphonium chloride, ethyltriphenylphosphonium bromide, methyltriphenylphosphonium bromide, tetrabutylphosphonium bromide and tetraphenylphosphonium bromide.

The phase transfer catalyst may also be a crown ether such as 15-crown-5, 18-crown-6, dibenzo-18-crown-6 and dicyclohexano-18-crown-6. Alternatively, the phase transfer catalyst may be a podand such as tris[2-(2-methoxyethoxy)ethyl]amine.

The phase transfer catalyst may also be a polyglycol, for example diethyleneglycol dibutyl ether, diethyleneglycol dimethyl ether, dipropyleneglycol dimethyl ether, ethyleneglycol dimethyl ether, polyethyleneglycol dibutyl ether, polyglycol BB 300, polyglycol DME 200, polyglycol DME 250, polyglycol DME 500, polyglycol DME 1000, polyglycol DME 2000, tetraethyleneglycol dimethyl ether and triethyleneglycol dimethyl ether.

A preferred process according to the present invention is schematically shown in Scheme 3 below.

Scheme 3

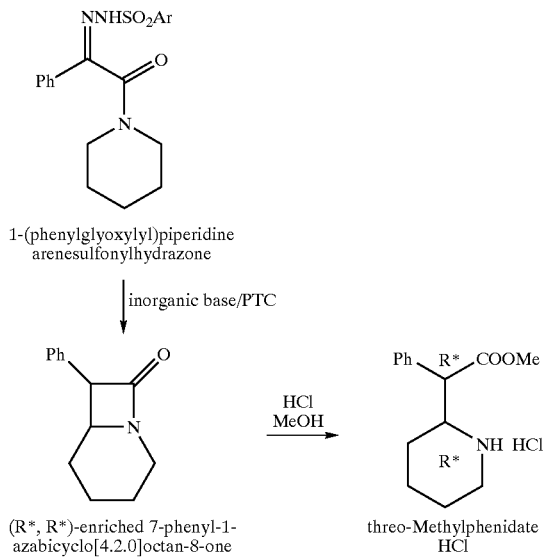

(R*, R*)-enriched 7-phenyl-1-azabicyclo[4.2.0]octan-8-one threo-Methylphenidate HCl The (R*,R*)-enriched 7-phenyl-1-azabicyclo[4.2.0]octan-8-one prepared in the first step is reacted with an acidified methanol solution. This reaction proceeds without epimerization, and the threo-enriched diastereomer of methylphenidate hydrochloride is formed, in high yields.

The desired pure threo-methylphenidate hydrochloride is obtained by crystallizing the threo-enriched methylphenidate hydrochloride. In the crystallization procedure, a suitable solvent and a co-solvent are chosen so as to avoid trans-esterification by-process that may occur. According to a preferred embodiment of the invention the solvent is methanol and the co-solvent is methyl tert-butyl ether. As shown in Scheme 4 below and described by Axten (1998) 1-(phenylglyoxylyl)piperidine arenesulfonylhydrazone may be readily prepared by a reaction of 1-(phenylglyoxylyl)piperidine with arenesulfonhydrazide and 1-(phenylglyoxylyl)piperidine may be prepared by reaction of piperidine with alkyl phenylglyoxylate.

Scheme 4

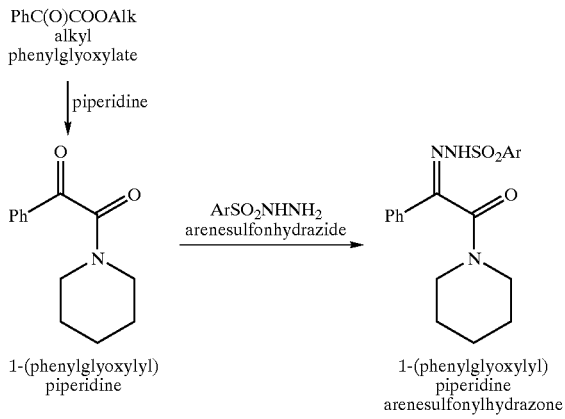

1-(phenylglyoxylyl) piperidine 1-(phenylglyoxylyl) piperidine arenesulfonylhydrazone The process of the invention uses commercially available or easily synthesized starting materials and it is thus amenable to laboratory scale (i.e. milligrams and grams), as well as industrial large-scale production (kilogram amounts, or more) of threo-methylphenidate. The large-scale production of threo-methylphenidate may require selection of reaction conditions, chemical process equipment, reactant quantities, reaction times, and the like, which are within the skill of the ordinary worker in the art.

EXAMPLES

In order to understand the invention and to see how it may be carried out in practice, preferred embodiments will now be described, by way of non-limiting examples only.

Example 1

1-(Phenylglyoxylyl)piperidine

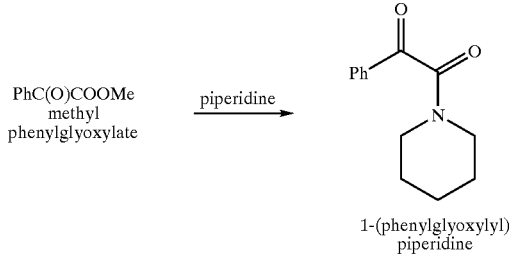

Methyl phenylglyoxylate (12.50 Kg, 76.1 mol, 1 eq) was added dropwise to a stirred mixture of piperidine (19.45 Kg, 228 mol, 3 eq) and methanol (5.0 L) for 3.5 hours to maintain the temperature at 45–55° C. The mixture was stirred at the same temperature for 0.5 hour and kept overnight at +4° C. The precipitated solid was filtered off, washed on the filter with cold methanol (5 L) and dried under reduced pressure to a constant weight to give 15.90 kg (96%) of 1-(phenylglyoxylyl)piperidine with 99.9% purity by GC.

Example 2

1-(Phenylglyoxylyl)piperidine p-toluenesulfonylhydrazone

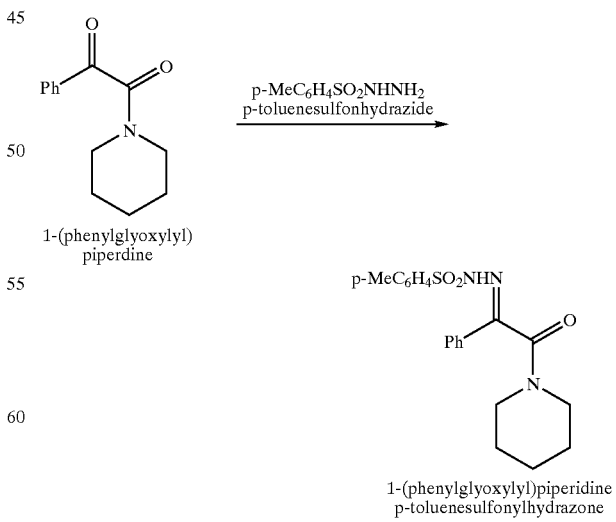

A solution of 98% sulfuric acid (121.7 g, 1.22 mol, 0.02 eq) in abs ethanol (1.0 L) was added dropwise to a stirred mixture of 1-(phenylglyoxylyl)piperidine (17.58 Kg, 80.9 mol, 1 eq), p-toluenesulfonhydrazide (16.20 Kg, 87.0 mol, 1.08 eq) and abs ethanol (50 L) at 20–30° C. The obtained mixture was stirred under reflux conditions until 1-(phenylglyoxylyl)piperidine disappeared (~7 hours, TLC control). The mixture was stirred for 1 hour at 20–30° C. and for 1 hour at 0–5° C. The precipitated solid was filtered off, washed on the filter with cold methanol and cold hexane and dried under reduced pressure to a constant weight to yield 28.25 Kg (90.6%) of 1-(phenylglyoxylyl)piperidine p-toluenesulfonylhydrazone with 99.9% purity by HPLC.

Example 3

(R*,R*)-Enriched 7-phenyl-1-azabicyclo[4.2.0]octan-8-one

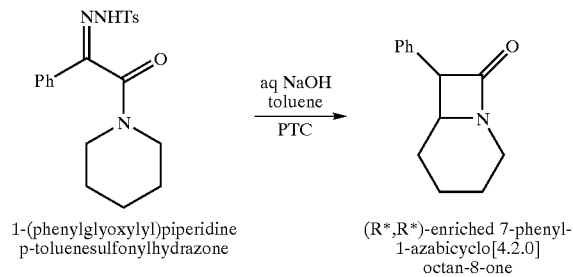

1-(phenylglyoxylyl)piperidine p-toluenesulfonylhydrazone → (R*,R*)-enriched 7-phenyl-1-azabicyclo[4.2.0]octan-8-one Sodium hydroxide, 50% aqueous solution (1.09 Kg, 13.6 mol, 1.05 eq) was added to a stirred mixture of 1-(phenylglyoxylyl)piperidine p-toluenesulfonylhydrazone (5.00 Kg, 13.0 mol, 1 eq), phase transfer catalyst (PTC) trioctylmethylammonium chloride (aliquat 336) (60.0 g, 0.15 mol, 0.01 eq) and toluene (50 L) at 20–30° C. The mixture was heated to reflux and monitored by both TLC and the color of the reaction mixture. The originally yellow solution in 10 minutes turned bright orange as the diazo compound was formed. After 6.5 hours at reflux, the solution re-assumed a yellow color and TLC indicated that no starting material was present. Crushed ice (20 Kg) was added to the reaction mixture (temperature of the mixture was dropped to 15° C.). The organic layer was separated, washed with brine (15 L) and evaporated under reduced pressure to give 2.69 Kg (quantitative yield) of 7-phenyl-1-azabicyclo [4.2.0]octan-8-one with R*R*/S*R* 3.3:1 by GC.

Example 4 threo-Enriched Methylphenidate

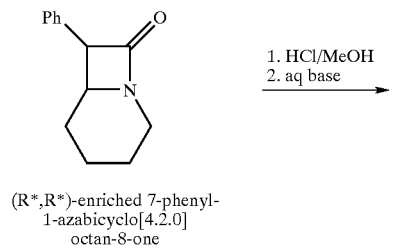

(R*,R*)-enriched 7-phenyl-1-azabicyclo[4.2.0]octan-8-one

1. HCl/MeOH
2. aq base

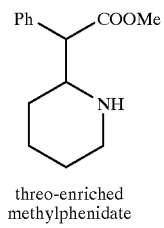

threo-enriched methylphenidate

Hydrogen chloride (gas) was passed through a stirred solution of 7-phenyl-1-azabicyclo [4.2.0]octan-8-one with R*R*/S*R* 3.3:1 by GC (2.61 Kg, 13.0 mol) in methanol (13 L) under reflux conditions for 60 hour until TLC indicated that all starting material has been consumed. The mixture was evaporated under reduced pressure. The residue was treated with hot water (8 L) for 0.5 h. The hot mixture was filtered, cooled to the room temperature, washed with toluene (2×1.2 L), basified with sodium carbonate to pH 10–11 and extracted with dichloromethane (2×2.5 L). The combined organic extracts were dried over sodium sulfate, filtered and evaporated under reduced pressure to give is 2.33 Kg (76.9%) of methylphenidate with threo/erythro 3.5:1 by GC.

Example 5 threo-Methylphenidate Hydrochloride

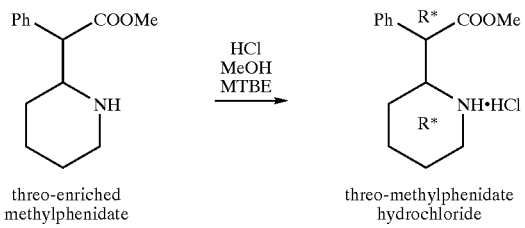

threo-enriched methylphenidate → threo-methylphenidate hydrochloride

Acetyl chloride (15.7 g, 0.2 mol, 1.0 eq) was added dropwise to a stirred methanol solution (150 mL) at 0–10° C. to form HCl in situ. The solution of methylphenidate, threo/erythro 3.5:1 by GC (46.7 g, 0.2 mol, 1.0 eq) in methanol (150 mL) was added dropwise to the obtained acidic solution at 0° C. The obtained solution was stirred under reflux conditions for 10 min. Methyl tert-butyl ether (MTBE) (300 mL) was added to the stirred solution at 50–60° C. The mixture was stirred for 2 hours at 20–30° C. and for 2 hours at −5–10° C. The precipitated solids were filtered off, washed on the filter with cold MTBE (400 mL) and dried under reduced pressure to give 31.1 g (58.2%) of threo-methylphenidate hydrochloride with 98.8% purity by GC (0.8% of erythro-isomer).

The invention claimed is:

1. A process for the preparation of threo-methylphenidate hydrochloride comprising: contacting 1-(phenylglyoxylyl) piperidine arenesulfonylhydrazone of the formula

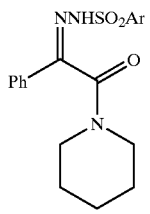

wherein Ar denotes an aryl group, where the aryl group may be substituted by a $C_1$–$C_6$ alkyl, halo or nitro group;
with an inorganic base in the presence of a water immiscible organic solvent and a phase transfer catalyst to obtain (R*,R*)-enriched 7-phenyl-1-azabicyclo[4.2.0]octan-8-one of the formula:

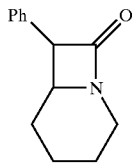

wherein said phase transfer catalyst is trioctylmethylammnonium chloride,
(i) reacting the (R*,R*)-enriched 7-phenyl-1-azabicyclo[4.2.0]octan-8-one with a solution of hydrogen chloride in methanol to obtain threo-enriched methylphenidate hydrochloride;
(ii) crystallizing the threo-enriched methylphenidate hydrochloride prepared in step (i) to give the hydrochloride salt of threo-methylphenidate containing 98.8% of the erythro-isomer.

2. The process of claim 1 wherein said water-immiscible organic solvent is selected from dichloromethane and toluene.

3. The process of claim 1 wherein said inorganic base is selected from sodium hydroxide, sodium carbonate, potassium carbonate or potassium hydroxide.

4. The process of claim 1 wherein said organic base is in solid form or in aqueous solution.

5. The process of claim 1 being carried out under reflux conditions.

6. The process of claim 1 wherein step (i) is carried out under reflux conditions.

* * * * *